United States Patent [19]

Stach

[11] 4,397,677
[45] Aug. 9, 1983

[54] DIOXOLANE SUBSTITUTED 2,6-DINITROANILINES

[75] Inventor: Leonard J. Stach, Riverside, Ill.

[73] Assignee: Velsicol Chemical Corporation, Chicago, Ill.

[21] Appl. No.: 204,446

[22] Filed: Nov. 6, 1980

Related U.S. Application Data

[63] Continuation-in-part of Ser. No. 98,563, Nov. 29, 1979, abandoned, which is a continuation-in-part of Ser. No. 44,619, Jun. 1, 1979, abandoned.

[51] Int. Cl.$^3$ .................................................. A01N 43/00
[52] U.S. Cl. ........................................ 71/88; 568/931; 549/451
[58] Field of Search ............... 568/931; 71/65, 88, 71/90; 260/340.9 R, 327 M, 561 HL; 424/269

[56] References Cited

U.S. PATENT DOCUMENTS

| | | | |
|---|---|---|---|
| 3,077,393 | 2/1963 | Howard et al. | 71/88 |
| 3,257,190 | 6/1966 | Soper | 71/121 |
| 3,518,076 | 6/1970 | Wright | 71/111 |
| 3,546,295 | 12/1970 | Maravetz | 260/577 |
| 3,555,045 | 1/1971 | Griffith et al. | 71/88 |
| 3,644,422 | 2/1972 | Mine et al. | 71/88 |
| 3,940,259 | 2/1976 | Richter et al. | 71/90 |
| 3,946,045 | 3/1976 | Richter et al. | 71/88 |
| 3,951,640 | 4/1976 | Krenzer | 71/90 |
| 4,012,222 | 3/1977 | Richter et al. | 71/88 |
| 4,022,608 | 5/1977 | Richter et al. | 71/88 |
| 4,046,758 | 9/1977 | Woods et al. | 71/88 |
| 4,113,464 | 9/1978 | Stach et al. | 71/88 |
| 4,118,216 | 10/1978 | Hotz et al. | 71/88 |
| 4,155,745 | 5/1979 | Walker | 71/88 |
| 4,166,908 | 9/1979 | Lutz et al. | 71/88 |
| 4,255,587 | 3/1981 | Plath et al. | 71/88 |
| 4,297,127 | 10/1981 | Lutz et al. | 71/88 |

FOREIGN PATENT DOCUMENTS

| | | | |
|---|---|---|---|
| 2258013 | 5/1973 | Fed. Rep. of Germany | 260/340.9 R |
| 1194727 | 6/1970 | United Kingdom | 71/88 |

OTHER PUBLICATIONS

Hall et al., J. Agricul. Food Chem., vol. 20, pp. 546–552 (1972), "Synthesis of Dinitroaniline . . . ".

Primary Examiner—Teddy S. Gron
Assistant Examiner—M. Moskowitz
Attorney, Agent, or Firm—Robert J. Schwarz

[57] ABSTRACT

This invention discloses new chemical compounds of the formula

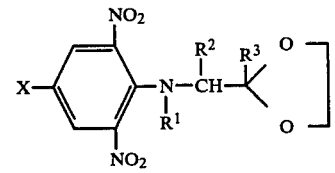

wherein $R^1$ is alkyl; $R^2$ and $R^3$ are hydrogen or alkyl; and X is selected from the group consisting of alkyl and haloalkyl, and their utility as herbicides.

13 Claims, No Drawings

DIOXOLANE SUBSTITUTED 2,6-DINITROANILINES

This application is a continuation-in-part of my copending application, Ser. No. 98,563, filed Nov. 29, 1979, now abandoned, which is a continuation-in-part of my copending application Ser. No. 44,619, filed June 1, 1979, now abandoned.

This invention relates to new compositions of matter and more specifically relates to new chemical compounds of the formula:

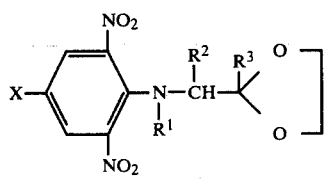
(I)

wherein $R^1$ is alkyl; $R^2$ and $R^3$ are independently selected from the group consisting of hydrogen and alkyl; and X is selected from the group consisting of alkyl and haloalkyl.

The compounds of the present invention are useful as herbicides and are particularly useful for the control of grassy weeds in such crops as soybeans.

In a preferred embodiment of the present invention $R^1$ is lower alkyl; $R^2$ and $R^3$ are hydrogen or lower alkyl; and X is selected from the group consisting of lower alkyl and lower alkyl and lower haloalkyl. The term lower as used herein designates a straight or branched carbon chain of up to six carbon atoms. In the most preferred embodiments of the present invention X is trifluoromethyl or t-butyl.

The compounds of the present invention can be prepared by reacting a compound of the formula

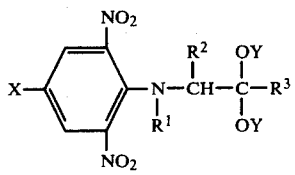
(II)

wherein X, $R^1$, $R^2$ and $R^3$ are as heretofore described and Y is methyl or ethyl, with ethylene glycol.

This reaction can be effected in the presence of a catalytic amount of para-toluenesulfonic acid. The reaction mixture, containing the reactants and catalyst in about equimolar amounts, can be heated to temperatures of about 100° C. to about 140° C. for from about 1 to about 8 hours. After this time, sodium carbonate is added to neutralize the catalyst. Ethyl acetate can be added and the mixture washed with water and dried over sodium sulfate. The desired product can be obtained after evaporation of the solvent used.

The compounds of formula II can be prepared by reacting a compound of the formula

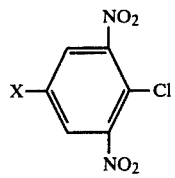
(III)

wherein X is as heretofore described, with a compound of the formula

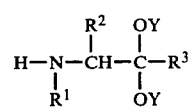
(IV)

wherein $R^1$, $R^2$, $R^3$ and Y are as heretofore described.

This reaction can be effected by heating a mixture of the two aforedescribed reactants in an inert reaction medium to reflux in the presence of an acid acceptor such as an alkali metal carbonate or bicarbonate or a tertiary amine. About equimolar amounts of the reactants can be effectively used. A reaction time of about one hour is sufficient to insure completion of the reaction.

The compounds of formula IV can be prepared by reacting an amine of the formula

(V)

wherein $R^1$ is as heretofore described, with a compound of the formula

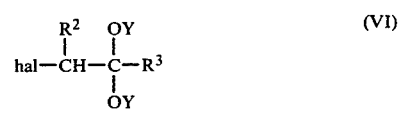
(VI)

wherein Y, $R^2$ and $R^3$ are as heretofore described and hal designates halogen, preferably chlorine or bromine.

This reaction can be effected by incrementally adding the compound of formula VI to a solution of the compound of formula V in an inert organic solvent such as dimethyl formamide at room temperature. About equimolar amounts of the reactants can be utilized. After the addition is completed, the reaction mixture can be heated under a nitrogen atmosphere at a temperature ranging up to the reflux temperature of the mixture for a period of up to about 50 hours. After this time water can be added to the reaction mixture and the mixture neutralized. The organic phase can be separated from the aqueous phase and can be stripped of solvent to yield the desired product.

The compounds of the present invention can also be prepared by reacting a compound of the formula

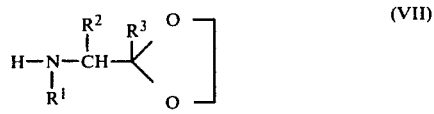
(VII)

wherein $R^1$, $R^2$ and $R^3$ are as heretofore described with a compound of formula III. This reaction may be effected by dissolving the compound of formula VII in an inert solvent, such as toluene and adding a slight excess molar amount of the compound of formula III in the presence of an acid acceptor such as a tertiary amine. The reaction mixture can then be heated at temperatures ranging up to the reflux temperature of the mixture. After completion of the reaction, the mixture can be washed with base and the desired product can be recovered upon stripping of the solvent used. The product can then be used as such or can be further purified by conventional techniques.

Exemplary compounds of formula III useful in preparing the compounds of this invention are 4-chloro-3,5-dinitrobenzotrifluoride, 4-chloro-3,5-dinitrotoluene and 4-chloro-3,5-dinitro-butylbenzene.

Exemplary compounds of formula IV in preparing the compounds of this invention are N-propyl-N-(2,2-dimethoxyethyl)amine, N-ethyl-N-(2,2-diethoxyethyl)amine, N-methyl-N-(2,2-diethoxyethyl)amine, N-butyl-N-(2,2-diethoxyethyl)amine, N-propyl-N-(1-methyl-2,2-dimethoxyethyl)amine, N-hexyl-N-(1-propyl-2,2-diethoxyethyl)amine and the like.

The manner in which the compound of this invention can be prepared is more specifically illustrated in the following examples.

EXAMPLE 1

Preparation of N-Propyl-N-(2,2-diethoxyethyl)amine

Propylamine (100 ml) and 1-bromo-2,2-diethoxyethane (50 ml) were charged into a glass reaction flask equipped with a stirrer, thermometer, heater and reflux condenser. The reaction mixture was then heated at reflux for a period of one hour with stirring. After this time the mixture is treated with 50% by weight aqueous sodium hydroxide and was then distilled under reduced pressure to yield the desired product N-propyl-N-(2,2-diethoxyethyl)amine.

EXAMPLE 2

Preparation of N-n-propyl-N-(2,2-diethoxyethyl)-2,6-dinitro-4-trifluoromethylaniline 4-Chloro-3,5-dinitrobenzotrifluoride (5.40 grams; 0.02 mol) was placed in a glass reaction flask containing N-n-propyl-N-2,2-diethoxyethylamine (3.5 grams; 0.02 mol), triethylamine (2.02 grams; 0.02 mol) and ethanol (100 ml) and equipped with stirrer, thermometer, heating mantle and reflux condenser. The mixture was heated at reflux for a period of about 1 hour. After this time the mixture was cooled and the solvent evaporated from the product. Benzene was added to the solid and the mixture was washed with water, dried over sodium sulfate and evaporated to give a dark oil (8.0 grams). This was chromatographed over silica gel by dissolving it in a 3:1 solution of benzene and ethylacetate. This product was then stripped of solvent to yield the desired product N-n-propyl-N-(2,2-diethoxyethyl)-2,6-dinitro-4-trifluoromethylaniline as an oil.

EXAMPLE 3

Preparation of N-Propyl-N-1,3-dioxolan-2-yl methyl-2,6-dinitro-4-trifluoromethylaniline N-(2,2-Diethoxyethyl)-N-propyl-2,6-dinitro-4-trifluoromethylaniline (5.5 grams; 0.0132 mol), ethylene glycol (0.84 grams; 0.0132 mole), p-toluenesulfonic acid (200 mg) and ethanol solvent were placed in a glass reaction flask equipped with stirrer, heating mantle and thermometer. The mixture was heated to 120° C. After the reaction was completed, the reaction mixture was cooled to room temperature, ethyl acetate was added and the mixture was washed with water and sodium bicarbonate solution. The solution was then dried over anhydrous magnesium sulfate and evaporated to yield the desired product N-propyl-N-1,3-dioxolan-2-ylmethyl-2,6-dinitro-4-trifluoromethylaniline as an oil.

EXAMPLE 4

Preparation of N-Methyl-N-(2,2-dimethoxyethyl)-2,6-dinitro-4-trifluoromethylaniline 4-Chloro-3,5-dinitrobenzotrifluoride (5.4 grams; 0.02 mole) dissolved in benzene was charged into a glass reaction vessel equipped with a mechanical stirrer and addition funnel. N-Methyl-N-2,2-dimethoxyethylamine (2,4 grams; 0.02 mole) and triethylamine (2.02 grams; 0.02 mole) both dissolved in benzene (50 ml) were then added dropwise with stirring. After the addition was completed stirring was continued for a period of 1 hour resulting in the formation of a precipitate. The reaction mixture was filtered to remove the acid acceptor salt and was chromatographed. The solution was then evaporated to yield a solid product. This solid was recrystallized from hexane to yield the desired product N-methyl-N-(2,2-dimethoxyethyl)-2,6-dinitro-4-trifluoroemethylaniline melting at 48° to 50° C.

EXAMPLE 5

Preparation of N-Methyl-N-1,3-dioxolan-2-ylmethyl-2,6-dinitro-4-trifluoromethylaniline N-Methyl-N-(2,2-dimethoxyethyl)-2,6-dinitro-4-trifluoromethylaniline (3.2 grams; 0.0915 mole), ethylene glycol 0.57 grams; 0.0915 mole), para-toluenesulfonic acid (200 mg) and ethyl acetate were charged into a glass reaction vessel equipped with a stirrer, heating mantle, reflux condenser and thermometer. The reaction mixture was heated at 120° C. with stirring for one hour. After this time the mixture was cooled to room temperature and washed with aqueous sodium bicarbonate. The washed solution was dried over anhydrous sodium sulfate, filtered and stripped of solvent leaving a solid residue. The residue was recrystallized from hexane to yield the desired N-methyl-N-1,3-dioxolan-2-ylmethyl-2,6-dinitro-4-trifluoromethylaniline as a yellow crystalline solid melting at 83° C.

EXAMPLE 6

Preparation of N-Ethyl-N-(2,2-diethoxyethyl)-amine

Ethylamine (38 grams) and 1-bromo-2,2-diethoxyethane (20 grams) were charged into a glass reaction vessel equipped with a mechanical stirrer, thermometer and reflux condenser. The reaction mixture was heated at reflux overnight. After this time the mixture was washed with aqueous sodium hydroxide and the organic phase separated from the aqueous phase. The organic phase was then distilled to yield the desired product N-ethyl-N-(2,2-diethoxyethyl)amine as an oil.

EXAMPLE 7

Preparation of N-Ethyl-N-(2,2-diethoxyethyl)-2,6-dinitro-4-trifluoromethylaniline 4-Chloro-3,5-dinitrobenzotrifluoride (5.4 grams; 0.02 mole) dissolved in toluene (50 ml) and a solution of N-ethyl-N-(2,2-diethoxyethyl)amine (3.2 grams; 0.02 mole) and triethylamine (2.02 grams; 0.02 mole in toluene (50 ml) were charged into a glass reaction vessel equipped with stirrer, thermometer and reflux condenser. The mixture was heated at reflux overnight resulting in the formation of a precipitate. The reaction mixture was then filtered and the filtrate was washed with water, dried and stripped of solvent to yield the desired product N-ethyl-N-(2,2-diethoxyethyl)-2,6-dinitro-4-trifluoromethylaniline.

EXAMPLE 8

Preparation of N-Ethyl-N-1,3-dioxolan-2-ylmethyl-2,6-dinitro-4-trifluoromethylaniline N-Ethyl-N-(2,2-diethoxyethyl)-2,6-dinitro-4-trifluoromethylaniline (6.10 grams; 0.0154 mole), ethylene glycol (0.96 grams; 0.0154 mole) and toluenesulfonic acid (200 mg) were charged into a glass reaction vessel equipped with stirrer and thermometer. The reaction mixture was heated at 110° C. for a period of 2 hours. After this time the mixture was cooled to room temperature, dissolved in ethyl acetate and washed with water and saturated aqueous sodium bicarbonate. The washed product was then dried and stripped of solvent to yield the desired product N-ethyl-N-1,3-dioxolan-2-ylmethyl-2,6-dinitro-4-trifluoromethylaniline as an oil.

EXAMPLE 9

Preparation of N-Ethyl-N-(2,2-diethoxyethyl)-2,6-dinitro-p-toluidine

4-Chloro-3,5-dinitrotoluene (4.32 grams; 0.02 mole), N-ethyl-N-(2,2-diethoxyethyl)amine (3.2 grams; 0.02 mole), triethylamine (2.02 grams; 0.02 mole) and toluene (100 ml) were charged into a glass reaction vessel equipped with a mechanical stirrer, thermometer and reflux condenser. The reaction mixture was heated at reflux overnight resulting in the formation of a precipitate. The reaction mixture was then filtered and the filtrate washed with water, dried and stripped of solvent to yield the desired product N-ethyl-N-(2,2-diethoxyethyl)-2,6-dinitro-p-toluidine.

EXAMPLE 10

Preparation of N-Ethyl-N-1,3-dioxolan-2-ylmethyl-2,6-dinitro-p-toluidine

N-Ethyl-N-(2,2-diethoxyethyl)-2,6-dinitro-p-toluidine (5.2 grams; 0.0132 mole), ethylene glycol (0.82 grams; 0.0132 mole) and toluenesulfonic acid (200 mg) were charged into a glass reaction vessel equipped with a mechanical stirrer and thermometer. The reaction mixture was heated at 110° C. for a period of one hour. After this time the mixture was dissolved in ethyl acetate and the resulting solution washed with aqueous base, dried and stripped of solvent to yield the desired product N-ethyl-N-1,3-dioxolan-2-ylmethyl-2,6-dinitro-p-toluidine as a brown oil.

EXAMPLE 11

4-Chloro-3,5-dinitrotoluene+N-propyl-N-(2,2-diethoxyethyl)amine+ethylene glycol=N-propyl-N-1,3-dioxolan-2-ylmethyl-2,6-dinitro-p-toluidine (dark oil).

EXAMPLE 12

4-Chloro-3,5-dinitrotoluene+N-methyl-N-(2,2-diethoxyethyl)amine+ethylene glycol=N-methyl-N-1,3-dioxolan-2-ylmethyl-2,6-dinitro-p-toluidine (brown oil).

EXAMPLE 13

4-Chloro-3,5-dinitrobenzotrifluoride+N-isopropyl-N-(2,2-deithoxyethyl)amine+ethylene glycol=N-isopropyl-N-1,3-dioxolan-2-ylmethyl-2,6-dinitro-4-trifluoromethylaniline (light yellow solid).

EXAMPLE 14

4-Chloro-3,5-dinitrobenzotrifluoride+N-propyl-N-(1-methyl-2,2-diethoxyethyl)amine+ethylene glycol=N-propyl-N-[1-(1,3-dioxolan-2-yl)ethyl]-2,6-dinitro-4-trifluoromethylaniline.

EXAMPLE 15

4-Chloro-3,5-dinitrobenzotrifluoride+N-methyl-N-(1-propyl-2,2-diethoxyethyl)amine+ethylene glycol+N-methyl-N-[1-(1,3-dioxolan-2-yl)-butyl]-2,6-dinitro-4-trifluoromethylaniline.

EXAMPLE 16

Preparation of N-ethyl-N-1,3-dioxolan-2-ylmethyl-2,6-dinitro-4-t-butylaniline 4-t-Butyl-2,6-dinitrochlorobenzene (1.8 grams; 0.007 mole), N-(1,3-dioxolan-2-yl)methyl ethylamine (1.83 grams; 0.014 mole) and toluene (50 ml) were placed in a glass reaction vessel equipped with a stirrer, heating mantle, reflux condenser and thermometer. The reaction mixture was heated to 90° C. and maintained at this temperature with stirring for 72 hours. Diethyl ether (50 ml) was added to the cooled reaction mixture, which was filtered and evaporated to a volume of 10 cc. The residue was chromatographed on silica to remove unreacted starting material. The product (1.7 grams) was obtained as an oil which solidified on standing (73°–74° C. melting point). The product was analyzed for $C_{16}H_{23}N_3O_6$:

|  | C | H | N |
| --- | --- | --- | --- |
| Calculated: | 54.38 | 6.56 | 11.89 |
| Found: | 54.23 | 6.91 | 11.89 |

EXAMPLE 17

Preparation of N-propyl-N-1,3-dioxolan-2-ylmethyl-2,6-nitro-4-t-butylaniline 4-t-Butyl-2,6-dinitrochlorobenzene (1.8 grams; 0.007 moles), N-(1,3-dioxolan-2-yl)methyl propylamine (2.02 grams (0.0014 mole) and toluene (50 ml) were placed in a glass reaction vessel equipped with a stirrer, heating mantle, reflux condenser and thermometer. The reaction mixture was heated to 90° C. and maintained at this temperature with stirring for 72 hours. Ethyl ether (50 ml) was added to the cooled reaction mixture, which was filtered and evaporated to a volume of 10 cc. The residue was chromatographed on silica to remove unreacted starting material. The product (1.2 grams) was obtained as a red oil.

The product was analyzed for $C_{16}H_{23}N_3O_6$:

|  | C | H | N |
|---|---|---|---|
| Calculated: | 55.57 | 6.86 | 11.44 |
| Found: | 55.42 | 7.01 | 11.36 |

EXAMPLE 18

Preparation of N-1,3-dioxolan-2-ylmethyl-2,6-dinitro-4-t-butylaniline 4-t-Butyl-2,6-dinitrochlorobenzene (1.8 grams; 0.007 mole), aminoacetaldehyde dimethyl acetal (1.5 grams; 0.0014 mole) and toluene (50 ml) were placed in a glass reaction vessel equipped with a stirrer, heating mantle, reflux condenser and thermometer and stirred overnight. Diethyl ether (50 ml) was added to the reaction mixture which was filtered and the filtrate then was evaporated. Toluene (50 ml), ethylene glycol (0.49 grams) and P-toluenesulfonic acid were added and the solution was refluxed for 2 hours. Then one-half the toluene was removed by distillation. The residue was chromatographed on silica to remove unreacted starting materials. The product (1.3 grams) was obtained as a yellow solid (melting point 81°–82° C.).

The product was analyzed for $C_{14}H_{19}N_3O_6$:

|  | C | H | N |
|---|---|---|---|
| Calculated: | 51.69 | 5.89 | 12.92 |
| Found: | 51.43 | 6.28 | 12.64 |

EXAMPLE 19

Preparation of N-1,3-Dioxolan-2-ylmethyl-2,6-dinitro-4-methyl aniline

N-(2,2-dimethoxyethyl)-2,6-dinitro-4-methylaniline (3.0 grams; 0.0105 mole), ethylene glycol (0.65 grams; 0.0105 mole), p-toluenesulfonic acid (200 mg) and ethanol solvent were placed in a glass reaction vessel equipped with a stirrer heating mantle and thermometer. The reaction mixture was heated to 110° C. and maintained at that temperature with stirring for one hour. Then the reaction mixture was cooled to room temperature, ethyl acetate has added and the mixture was washed with water and sodium bicarbonate solution. The solution was dried over anhydrous magnesium sulfate and evaporated to yield the desired product (2.0 grams) of a yellow oil. The product was analyzed for $C_{11}H_{10}N_3O_6$:

|  | C | H | N |
|---|---|---|---|
| Theoretical | 46.64 | 4.63 | 14.84 |
| Found | 46.88 | 4.62 | 15.31 |

EXAMPLE 20

Preparation of 2-methyl-2-bromomethyl-1,3-dioxolane

Bromoacetone (80 grams; 0.58 mole), ethylene glycol (37.2 grams; 0.06 mole) toluene (250 ml) and p-toluenesulfonic acid (400 mg) were placed in a glass reaction vessel equipped with a stirrer and thermometer. The mixture was heated with stirring on a hot oil bath to 120° C. until volatile material did not continue to be released from the mixture. Then the temperature was raised to 140° C. for 4 hours and the mixture neutralized by the addition of sodium carbonate (5 grams). The mixture was then washed with water, and dried over anhydrous magnesium sulfate. A brown oil (102 grams) was obtained which was distilled with sodium carbonate. The desired product was confirmed by nuclear magnetic resonance.

EXAMPLE 21

Preparation of 2-(ethylamino)methyl-2-methyl-1,3-dioxolane

Ethylamine (115 grams; 1.77 mole) and 2-methyl-2-bromomethyl-1,3-dioxolane (32 grams; 0.177 mole) were placed in a stainless steel bomb and placed on a steam bath for 5 hours. The temperature of the mixture was raised to 120° C. for 15 hours. The mixture was cooled and ether (200 ml) added to it. Sodium hydroxide (25 grams) was added and the ether layer separated and dried over magnesium sulfate. The ether was evaporated leaving the desired product (10.3 grams) as identified by nuclear magnetic resonance.

EXAMPLE 22

Preparation of N-ethyl-(2-methyl-1,3-dioxolane-2-yl)methyl-4-t-butyl-2,6-dinitroaniline 4-t-butyl-2,6-dinitro chlorobenzene (2.5 grams; 0.01 mole), 2-(ethylamino)methyl-2-methyl-1,3-dioxolane (2.9 grams; 0.02 mole) and toluene (50 ml) were placed into a glass reaction vessel equipped with a stirrer, oil bath and thermometer and heated to 70° C. with stirrer for 30 hours. Ethanol (50 ml) was added to the cooled mixture and the solid filtered therefrom. The filtrate was evaporated to a volume of approximately 10 ml. It was then chromatographed on silica gel to yield the desired product (2.0 grams). The product was analyzed for $C_{17}H_{25}N_3O_6$:

|  | C | H | N |
|---|---|---|---|
| Calculated: | 55.57 | 6.86 | 11.44 |
| Found: | 55.15 | 6.99 | 11.24 |

Further compounds within the present invention are examplified by the following:

N-ethyl-N-1,3-dioxolan-2-ylmethyl-2,6-dinitro-4-ethoxyaniline
N-but-2-enyl-N-1,3-dioxolan-2-ylmethyl-2,6-dinitro-4-propoxyaniline
N-pent-4-enyl-N-1,3-dioxolan-2-ylmethyl-2,6-dinitro-4-hexyloxyaniline
N-hex-4-enyl-N-1,3-dioxolan-2-ylmethyl-2,6-dinitro-4-trichloromethylaniline
N-propyl-N-1,3-dioxolan-2-ylmethyl-2,6-dinitro-4-bromomethylaniline
N-propyl-N-1,3-dioxolan-2-ylmethyl-2,6-dinitro-4-β-isodoethylaniline
N-propyl-N-1,3-dioxolan-2-ylmethyl-2,6-dinitro-4-δ,δ,δ-trichlorobutylaniline
N-propyl-N-1,3-dioxolan-2-ylmethyl-2,6-dinitro-4-ω-chlorohexylaniline For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by inpregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifiers systems an inverted emulsion (water in oil) can be prepared for direct application to weed infestations.

A typical herbicidal composition according to this invention is ilustrated by the following example, in which the quantities are in parts by weight.

EXAMPLE 20

Preparation of a Dust

Product of Example 3: 10
Powdered Talc: 90

The above ingredients are mixed in a mechanical grinder-blender and are ground unitl a homogeneous, freeflowing dust of the desired particle size as obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore descrived. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPA, 4-CPP, 2,4,5-TB, 2,4,5-TES, 3,4-DA, silvex and the like, carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, kinuron, monolinuron, neburon, buturon, trimeturon and the like; symmetrical triazine herbicides such as simazine, chlorazine, atraone, desmetryne, norazine, ipazine, prometryn, atrazine, treitazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)morpholine, 1-(chloracetyl)piperdine, and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-cichloro-3-nitrobenzoic acid and the like; such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin; trifluralin, dolan, dicryl, merphos, DMPA, DSMA, MSMA, potassium azide, acrolein, benefin, bensulfide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMIT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, tcba, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose-grass, chickweed, wild oats, velvet leaf purselane, barnyard grass, smartweed, knotweed, cocklebur, wild buckwheat, kochia, medic, corn cockle, ragweed, sowthistle, coffee-weed, croton, cuphea, dodder, fumitory, groundsel, hemp nettle, knowel, spurg, spurry, emex, jungle rice, pondweed, dog fennel, carpetweed, morningglory, bedstraw, ducksalad and naiad; biennials such as wild carrot, matricaria, wild barley, campion, chamomile, burdock, mullein, roundleaved mallow, bull thistle, hounds-tongue, moth mullein, and purple star thistle; or perennials such as white cockle, perennial ryegrass, quack-grass, Johnson grass, Canada thistle, hedge bindweed, Bermuda grass, sheep sorrel, curly dock, nutgrass, field chickweed, dandelion, campanyla, field bindweed, Russian knapweed, mesquite, toadflax, yarrow, aster, gromwell, horsetail, ironweed, sesbania, bulrush, cattail and winter-cress.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after seeding the pots were sprayed with water until the soil was wet and these compounds dissolved in a solvent comprising a mixture of 45 volumes acetone 2, volumes methanol and one volume N,N-dimethyl formamide were sprayed at the indicated concentrations on the surface of the soil.

After spraying, the soil containers were placed in the greenhouse and provided with supplementary heat as required and daily or more frequent watering. The plants were maintained under these conditions for a period of from 14 to 21 days, at which time the condition of the plants and the degree of injury to the plants was rated on a scale of from 0 to 10 as follows: 0=no injury, 1,2=slurry injury, 3,4=moderate injury, 5,6=moderately severe injury, 7,8,9=severe injury and 10=death. N.E. indicates no emergence of the plant from the soil. The effectiveness of these compounds is demonstrated by the data in Table I, below.

The herbicidal activity of the compounds of this invention was also demonstrated by experiments carried out for the post-emergence control of a variety of weeds. In these experiments the compounds to be tested were formulated as aqueous emulsions and sprayed at the indicated dosage on the foliage of the weeds that have attained a prescribed size. After spraying the plants were placed in a greenhouse and watered daily or more frequently. Water was not applied to the foliage of the treated plants. The severity of the injury was determined 14 days after treatment and was rated on the scale of from 0 to 10 heretofore described. The effectiveness of these compounds is demonstrated by the date in Table II, below.

In both Tables I and II the following abbreviations for the various weed species and crop species were used:

| | |
|---|---|
| ABLUE | Annual Bluegrass |
| ALFA | Alfalfa |
| BDWD | Bindweed |
| BNGS | Barnyardgrass |
| CBGS | Crabgrass |
| CORN | Corn |
| COTN | Cotton |
| CTGS | Cheatgrass (Downy Brome) |
| JMWD | Jimsonweed |
| JNGS | Johnsongrass |
| MBLUE | Merion Bluegrass |
| MNGY | Morningglory, Annual |
| OAT | Oat |
| PIGW | Pigweed |
| PTBN | Pintobean |
| PYRE | Perennial Ryegrass |
| QKGS | Quackgrass |
| RICE | Rice |
| SORG | Sorghum |
| SOYB | Soybean |
| SPGT | Sprangletop |
| SUBT | Sugar Beet |
| TFES | Tall Fescue |
| VTLF | Velvetleaf |
| WHT | Wheat |
| WMSTD | Wild Mustard |
| WOAT | Oats, Wild |
| YLFX | Foxtail, Yellow |
| YNSG | Nutsedge, Yellow |

TABLE I

Injury Rating - Pre-Emergence

| TEST COMPOUND | RATE lbs/Acre | TIME AFTER TREATMENT (Days) | Weed Species |||||||||
|---|---|---|---|---|---|---|---|---|---|---|---|
| | | | YNSG | WOAT | JMWD | VTLF | JNGS | PIGW | WMSTD | YLFX | BNGS |
| Product of Ex. 3 | 8 | 14 | NE | 9 | NE | 6 | 9 | 9 | 7 | 9 | 10 |
| " | 2 | 14 | 5 | 7 | 0 | 2 | 8 | 8 | 2 | 9 | 10 |
| " | 1 | 14 | 5 | 6 | 2 | 3 | 7 | 5.3 | 2 | 9 | 10 |
| " | 0.5 | 14 | — | 3 | 2 | 0 | 6 | 0 | 1.7 | 9 | 10 |

TABLE I-continued

Injury Rating - Pre-Emergence

| TEST COMPOUND | RATE lbs/Acre | TIME AFTER TREATMENT (Days) | SORG | WOAT | PTBN | CORN | JNGS | QKGS | ALFA | OAT | SPGT |
|---|---|---|---|---|---|---|---|---|---|---|---|
| " | 0.25 | 14 | — | 3 | 0 | 0 | 5 | 1.3 | 1.3 | 8 | 9 |
| " | 0.125 | 14 | — | 1.3 | 1 | 0 | 3.3 | 1.3 | 1 | 7 | 6 |
| " | 8 | 21 | NE | 9 | 8 | 8 | 9 | 9 | 8 | 9 | 10 |
| " | 2 | 21 | 4 | 7 | 0 | 4 | 6 | 8 | 2 | 9 | 10 |
| " | 1 | 21 | 0 | 5 | 1 | 2 | 6.2 | 6.2 | 3 | 9 | 10 |
| " | 0.5 | 21 | — | 2.3 | 0 | 0 | 8 | 1 | 3.3 | 9 | 10 |
| " | 0.25 | 21 | — | 1 | 0 | 0 | 4.3 | 1 | 4 | 8.2 | 6 |
| " | 0.125 | 21 | — | 0 | 0 | 0 | 2.3 | 1.3 | 3.3 | 5 | 6 |
| Product of Ex. 5 | 8 | 14 | 2 | 4 | 9 | 6 | NE | 8 | 5 | 9 | 9 |
| " | 2 | 14 | 1 | 4 | 0 | 8 | NE | 6 | 3 | 9 | 9 |
| " | 1 | 14 | 0 | 0 | 0 | NE | 0 | 6 | 4 | 4 | 8 |
| " | 0.5 | 14 | — | — | — | — | — | — | — | — | — |
| " | 0.25 | 14 | — | — | — | — | — | — | — | — | — |
| " | 0.125 | 14 | — | — | — | — | — | — | — | — | — |
| " | 8 | 21 | 1 | 6 | 2 | 4 | 4 | 3 | 7 | 7 | 10 |
| " | 2 | 21 | 0 | 4 | 0 | 7 | 6 | 3 | 2 | 7 | 10 |
| " | 1 | 21 | 0 | 2 | 0 | NE | 5 | 4 | 4 | 4 | 6 |
| " | 0.5 | 21 | — | — | — | — | — | — | — | — | — |
| " | 0.25 | 21 | — | — | — | — | — | — | — | — | — |
| " | 0.125 | 21 | — | — | — | — | — | — | — | — | — |
| Product of Ex. 8 | 8 | 14 | 8 | 10 | 8 | 8 | 6 | 10 | 8 | 10 | 10 |
| " | 2 | 14 | 5 | 7.3 | 4 | 6 | 9.3 | 9 | 4 | 9.3 | 10 |
| " | 1 | 14 | 1 | 6 | 6.2 | 4 | 9 | 6 | 2.2 | 9 | 9.2 |
| " | 0.5 | 14 | — | 6 | 6 | 1 | 7 | 4 | 0 | 8 | 10 |
| " | 0.25 | 14 | — | 5 | 6 | 0 | 7 | 2 | 0 | 6 | 9 |
| " | 0.125 | 14 | — | 4 | 3 | 0 | 5 | 0 | 2 | 5 | 4 |
| " | 8 | 21 | 8 | 10 | 8 | 9 | 10 | 10 | 9 | 10 | 10 |
| " | 2 | 21 | 3 | 9 | 4.3 | 2.3 | 10 | 9 | 3 | 9.3 | 10 |
| " | 1 | 21 | 0 | 7 | 6 | 6 | 9 | 6 | 2 | 9 | 9 |
| " | 0.5 | 21 | — | 5 | 4 | 0 | 7 | 3 | 1 | 7 | 10 |
| " | 0.25 | 21 | — | 3 | 4 | 0 | 6 | 1 | 0 | 6 | 10 |
| " | 0.125 | 21 | — | 0 | 0 | 0 | 6 | 0 | 2 | 4 | 3 |
| Product of Ex. 10 | 8 | 14 | 6 | 8 | 7 | 7 | 9 | 9 | 8 | NE | NE |
| " | 2 | 14 | 0 | 7 | 7 | 6 | 9 | 9 | 7 | 10 | NE |
| " | 1 | 14 | 0 | 6 | 7 | 1 | 9 | 8 | 2 | 8 | 10 |
| " | 0.5 | 14 | — | 5 | 9 | 0 | 6 | 8 | 1 | 6 | 9 |
| " | 0.25 | 14 | — | 3 | NE | 0 | 5 | 3 | 0 | 2 | 9 |
| " | 0.125 | 14 | — | — | — | — | — | — | — | — | — |
| " | 8 | 21 | 7 | 10 | 8 | 9 | 10 | 9 | 8 | 10 | 10 |
| " | 2 | 21 | 0 | 8 | 6 | 4 | 8 | 10 | 8 | 10 | 10 |
| " | 1 | 21 | 0 | 7 | 6 | 2 | 8 | 9 | 2 | 7 | 10 |
| " | 0.5 | 21 | — | 2 | 4 | 1 | 6 | 9 | 0 | 5 | 10 |
| " | 0.25 | 21 | — | 2 | NE | 1 | 0 | 2 | 0 | 0 | 7 |
| " | 0.125 | 21 | — | — | — | — | — | — | — | — | — |
| Product of Ex. 11 | 8 | 14 | NE | 7 | 7 | 7 | 9 | NE | 8 | 9 | 10 |
| " | 2 | 14 | NE | 6 | 0 | 4 | 9 | 8 | 2 | 9 | 10 |
| " | 1 | 14 | 9 | 2 | 0 | 1 | 7 | 4 | 0 | 9 | 10 |
| " | 0.5 | 14 | — | — | — | — | — | — | — | — | — |
| " | 0.25 | 14 | — | — | — | — | — | — | — | — | — |
| " | 0.125 | 14 | — | — | — | — | — | — | — | — | — |
| " | 8 | 21 | 9 | 10 | 7 | 9 | 10 | 10 | 9 | 1 | 10 |
| " | 2 | 21 | NE | 6 | 0 | 6 | 9 | 8 | 5 | 9 | 10 |
| " | 1 | 21 | 6 | 3 | 1 | 2 | 7 | 3 | 0 | 7 | 10 |
| " | 0.5 | 21 | — | 0 | 3 | 1 | — | 5 | 0 | 1 | 9 |
| " | 0.25 | 21 | — | 0 | 0 | 0 | — | 0 | 0 | 0 | 3 |
| " | 0.125 | 21 | — | — | — | — | — | — | — | — | — |
| Product of Ex. 12 | 8 | 14 | 2 | 6 | 6 | 5 | 7 | 8 | 7 | NE | NE |
| " | 2 | 14 | 0 | 3 | 4 | 0 | 6 | 0 | 2 | 8 | 9 |
| " | 1 | 14 | 3 | 1 | 0 | 0 | 0 | 0 | 0 | 4 | 5 |
| " | 0.5 | 14 | — | — | — | — | — | — | — | — | — |
| " | 0.25 | 14 | — | — | — | — | — | — | — | — | — |
| " | 0.125 | 14 | — | — | — | — | — | — | — | — | — |
| " | 8 | 21 | 2 | 7 | 4 | 5 | 9 | 8 | 7 | 10 | 10 |
| " | 2 | 21 | 0 | 2 | 0 | 2 | 5 | 0 | 0 | 7 | 10 |
| " | 1 | 21 | 2 | 0 | 0 | 0 | 0 | 0 | 0 | 0 | 0 |
| " | 0.5 | 21 | — | — | — | — | — | — | — | — | — |
| " | 0.25 | 21 | — | — | — | — | — | — | — | — | — |
| " | 0.125 | 21 | — | — | — | — | — | — | — | — | — |
| Product of Ex. 13 | 8 | 14 | — | — | — | — | — | — | — | — | — |
| " | 2 | 14 | — | — | — | — | — | — | — | — | — |
| " | 1 | 14 | — | — | 4 | 2 | — | 3 | 2 | 9 | 10 |
| " | 0.5 | 14 | — | — | 2 | 0 | — | NE | 0 | 8 | 8 |
| " | 0.25 | 14 | — | — | 0 | 0 | — | 0 | 0 | 7 | 3 |
| " | 0.125 | 14 | — | — | 0 | 0 | — | 0 | 0 | 4 | 3 |
| Product of Ex. 13 | 8 | 21 | — | — | — | — | — | — | — | — | — |
| " | 2 | 21 | — | — | — | — | — | — | — | — | — |
| " | 1 | 21 | 6 | 5 | 2 | 5 | 7 | NE | 0 | 4 | NE |

TABLE I-continued

| | | | | | | | | | | | |
|---|---|---|---|---|---|---|---|---|---|---|---|
| Injury Rating - Pre-Emergence | | | | | | | | | | | |
| " | 0.5 | 21 | 7 | 3 | 2 | 3 | 7 | NE | 0 | 2 | NE |
| " | 0.25 | 21 | 2 | 0 | 0 | 3 | 3 | 4 | 0 | 0 | 7 |
| " | 0.125 | 21 | 4 | 1 | 0 | 3 | 2 | 4 | 0 | 2 | 6 |

| TEST COMPOUND | RATE lbs/Acre | TIME AFTER TREATMENT (Days) | Weed Species | | | | | | | | |
|---|---|---|---|---|---|---|---|---|---|---|---|
| | | | YNSG | WOAT | JMWD | VTLF | JNGS | PIGW | WMSTD | YLFX | BNGS |
| Product of Ex. 16 | 8 | 14 | 0 | 7 | 2 | 8 | 9 | 8 | 7 | NE | NE |
| " | 1 | 14 | 5 | 2 | NE | NE | 5 | NE | 6 | NE | NE |
| " | 0.5 | 14 | — | 2 | NE | 0 | 6 | 3 | 7 | NE | NE |
| " | 0.25 | 14 | — | 2 | 0 | 0 | 4 | 0 | 1 | NE | NE |
| " | 0.125 | 14 | — | 0 | NE | 0 | 0 | 0 | 0 | NE | NE |
| " | 8 | 21 | 0 | 7 | 5 | 8 | 9 | 7 | 9 | NE | NE |
| " | 1 | 21 | — | 5 | 1 | 9 | 7 | NE | — | — | NE |
| " | 0.5 | 21 | — | 2.3 | NE | 1 | 6 | 6 | — | — | NE |
| " | 0.25 | 21 | — | 1 | 0 | 0 | 5 | 0 | — | — | NE |
| " | 0.125 | 21 | — | 0 | NE | 0 | 0 | 0 | — | — | 7 |
| Product of Ex. 17 | 8 | 21 | 0 | 9 | 2 | 8 | 9 | 9 | 8 | NE | NE |
| " | 1 | 21 | — | NE | 3 | NE | 9 | NE | — | — | NE |
| " | 0.5 | 21 | — | 0 | NE | 0 | 10 | 2 | — | — | 10 |
| " | 0.25 | 21 | — | 1 | 0 | 0 | 6 | 2 | — | — | 10 |
| " | 0.125 | 21 | — | 0 | 0 | 0 | 3 | 0 | — | — | 8 |
| Product of Ex. | 8 | 14 | 0 | 7 | 0 | 7 | 8 | NE | 3 | NE | NE |
| " | 1 | 14 | 5 | NE | 5 | NE | 8 | NE | 0 | NE | NE |
| " | 0.5 | 14 | — | 1 | NE | 0 | 7 | 0 | 0 | NE | 10 |
| " | 0.25 | 14 | — | 0 | 0 | 0 | 5 | 0 | 0 | NE | 10 |
| " | 0.125 | 14 | — | 0 | 0 | 0 | 3 | 0 | 0 | NE | 10 |
| Product of Ex. 18 | 8 | 14 | 0 | 3 | 3 | 0 | 7 | 9 | 3 | 9 | 10 |
| " | 8 | 21 | 0 | 0 | 0 | 0 | 2 | 0 | 0 | 0 | 0 |
| Product of Ex. | 8 | 14 | 5 | 4 | NE | 2 | 7 | 8 | 10 | 9 | 10 |
| " | 2 | 14 | 0 | 0 | 0 | 0 | 0 | 4 | 0 | 4 | 3 |
| " | 1 | 14 | 0 | 0 | 2 | 0 | 0 | 0 | 0 | 0 | 3 |
| Product of Ex. 19 | 8 | 21 | 3 | 2 | NE | 3 | 7 | 7 | 10 | 8 | 10 |
| " | 2 | 21 | 0 | 0 | 0 | 0 | 0 | 0 | 0 | 3 | 2 |
| " | 1 | 21 | 5 | 0 | 0 | 0 | 0 | 0 | 0 | 1 | 0 |
| Product of Ex. 22 | 8 | 14 | — | — | — | — | — | — | — | — | — |
| " | 1 | 14 | 5 | 3 | 9 | 1 | 7 | 9 | 2 | NE | 9 |
| " | 0.5 | 14 | — | 1 | 1 | 0 | 4 | 0 | 2 | NE | 7 |
| " | 0.25 | 14 | — | 0 | 0 | 0 | 0 | 0 | 0 | NE | 10 |
| " | 0.125 | 14 | — | 0 | 0 | 0 | 0 | 0 | 0 | NE | 10 |
| " | 8 | 21 | 8 | 6 | NE | 5 | 8 | — | 7 | NE | NE |
| " | 1 | 21 | — | 1 | 3 | 3 | 5 | 9 | 0 | — | 10 |
| " | 0.5 | 21 | — | 0 | 0 | 0 | 4 | 0 | 0 | — | 10 |
| " | 0.25 | 21 | — | 0 | 0 | 0 | 0 | 0 | 0 | — | 10 |
| " | 0.125 | 21 | — | 0 | 0 | 0 | 0 | 0 | — | — | 10 |

| TEST COMPOUND | RATE lbs/Acre | TIME AFTER TREATMENT (Days) | Weed Species | | | | | | | | |
|---|---|---|---|---|---|---|---|---|---|---|---|
| | | | CBGS | CTGS | MNGY | BDWD | MBLUE | TFES | PYRE | SUBT | WHT |
| Product of Ex. 3 | 8 | 14 | NE | NE | 6 | — | — | — | — | — | — |
| " | 2 | 14 | 9 | NE | 4 | — | — | — | — | — | — |
| " | 1 | 14 | 10 | 7 | 4 | 5.3 | NE | 10 | NE | 2.6 | 8 |
| " | 0.5 | 14 | 9.1 | 4.3 | 2 | 1.3 | NE | 7 | 10 | .3 | 4.3 |
| " | 0.25 | 14 | 7.2 | 3 | 1.3 | 1 | 9 | 6 | 7 | 0 | 2.3 |
| " | 0.125 | 14 | 7.1 | 1 | 0 | 1 | 8 | 5 | 5 | .3 | 1 |
| " | 8 | 21 | 9 | NE | 8 | — | — | — | — | — | — |
| " | 2 | 21 | 9 | 0 | 4 | — | — | — | — | — | — |
| " | 1 | 21 | 10 | 8 | 3.3 | 6 | 10 | 10 | NE | 2 | 7 |
| " | 0.5 | 21 | 10 | 5 | 3 | 2 | 10 | 7.2 | 10 | 1 | 4 |
| " | 0.25 | 21 | 7 | 0 | 1.3 | 1.6 | 8.2 | 6 | 6.2 | 1 | 1 |
| " | 0.125 | 21 | 6 | 0 | 1 | 1.3 | 8 | 6 | 3 | 0 | .3 |
| Product of Ex. 5 | 8 | 14 | NE | NE | 3 | | | | | | |
| " | 2 | 14 | NE | 9 | 2 | | | | | | |
| " | 1 | 14 | NE | 4 | 1 | | | | | | |
| " | 0.5 | 14 | — | — | — | | | | | | |
| " | 0.25 | 14 | — | — | — | | | | | | |
| " | 0.125 | 14 | — | — | — | | | | | | |
| " | 8 | 21 | NE | 0 | 4 | | | | | | |
| " | 2 | 21 | NE | 9 | 5 | | | | | | |
| " | 1 | 21 | NE | 3 | 4 | | | | | | |
| " | 0.5 | 21 | — | — | — | | | | | | |
| " | 0.25 | 21 | — | — | — | | | | | | |
| " | 0.125 | 21 | — | — | — | | | | | | |
| Product of Ex. 8 | 8 | 14 | 10 | 10 | 7 | — | — | — | — | — | — |
| " | 2 | 14 | 9.3 | 10 | 6 | 9 | — | — | — | 8 | 9 |
| " | 1 | 14 | 8 | 10 | 3 | 5 | — | — | — | 3 | 9 |
| " | 0.5 | 14 | 8 | 8 | 2 | 5 | — | — | — | 0 | 8 |
| " | 0.25 | 14 | 7 | 8 | 4 | 3 | — | — | — | 0 | 5 |
| " | 0.125 | 14 | 6 | 0 | 2 | 2 | — | — | — | 0 | 5 |

TABLE I-continued

Injury Rating - Pre-Emergence

| | | | | | | | | | | | |
|---|---|---|---|---|---|---|---|---|---|---|---|
| " | 8 | 21 | 10 | 10 | 10 | — | — | — | — | — | — |
| " | 2 | 21 | 9.3 | 10 | 7 | 8 | — | — | — | 8 | 9 |
| " | 1 | 21 | 8 | 9 | 3 | 6 | — | — | — | 4 | 9 |
| " | 0.5 | 21 | 8 | 8 | 0 | 5 | — | — | — | 0 | 8 |
| " | 0.25 | 21 | 7 | 7 | 0 | 2 | — | — | — | 0 | 2 |
| " | 0.125 | 21 | 6 | 0 | 0 | 0 | — | — | — | 0 | 3 |
| Product of Ex. 10 | 8 | 14 | NE | NE | 7 | — | — | — | — | — | — |
| " | 2 | 14 | 10 | 10 | 6 | 9 | — | — | — | 9 | 9 |
| " | 1 | 14 | 10 | 9 | 5 | 8 | — | — | — | 9 | 9 |
| " | 0.5 | 14 | 9 | NE | 4 | 8 | — | — | — | 5 | 5 |
| " | 0.25 | 14 | 8 | NE | 0 | 1 | — | — | — | 0 | 3 |
| " | 0.125 | 14 | — | — | — | — | — | — | — | — | — |
| " | 8 | 21 | 10 | 10 | 9 | — | — | — | — | — | — |
| " | 2 | 21 | 7 | 10 | 7 | 9 | — | — | — | 9 | 10 |
| " | 1 | 21 | 10 | 8 | 6 | 7 | — | — | — | 9 | 10 |
| " | 0.5 | 21 | 9 | NE | 4 | 6 | — | — | — | 6 | 2 |
| " | 0.25 | 21 | 7 | NE | 0 | 3 | — | — | — | 0 | 0 |
| " | 0.125 | 21 | — | — | — | — | — | — | — | — | — |
| Product of Ex. 11 | 8 | 14 | NE | NE | 7 | | | | | | |
| " | 2 | 14 | NE | NE | 5 | | | | | | |
| " | 1 | 14 | 9 | 7 | 1 | | | | | | |
| " | 0.5 | 14 | — | — | — | | | | | | |
| " | 0.25 | 14 | — | — | — | | | | | | |
| " | 0.125 | 14 | — | — | — | | | | | | |
| " | 8 | 21 | 10 | 10 | 10 | — | — | — | — | — | — |
| " | 2 | 21 | 5 | 10 | 8 | 8 | — | — | — | 6 | 1 |
| " | 1 | 21 | 9 | 9 | 4 | 4 | — | — | — | 5 | 3 |
| " | 0.5 | 21 | 7 | NE | — | 0 | — | — | — | 5 | 0 |
| " | 0.25 | 21 | 2 | NE | — | 0 | — | — | — | 0 | 0 |
| " | 0.125 | 21 | — | — | — | — | — | — | — | — | — |
| Product of Ex. 12 | 8 | 14 | NE | NE | 6 | | | | | | |
| " | 2 | 14 | 9 | 6 | 2 | | | | | | |
| " | 1 | 14 | 7 | 0 | 0 | | | | | | |
| " | 0.5 | 14 | — | — | — | | | | | | |
| " | 0.25 | 14 | — | — | — | | | | | | |
| " | 0.125 | 14 | — | — | — | | | | | | |
| " | 8 | 21 | 10 | 10 | 6 | | | | | | |
| " | 2 | 21 | 9 | 3 | 2 | | | | | | |
| " | 1 | 21 | 4 | 0 | 1 | | | | | | |
| " | 0.5 | 21 | — | — | — | | | | | | |
| " | 0.25 | 21 | — | — | — | | | | | | |
| " | 0.125 | 21 | — | — | — | | | | | | |
| Product of Ex. 13 | 8 | 14 | — | — | — | — | — | — | — | — | — |
| " | 2 | 14 | — | — | — | — | — | — | — | — | — |
| " | 1 | 14 | — | — | — | 3 | — | — | — | 0 | 8 |
| " | 0.5 | 14 | — | — | — | 2 | — | — | — | 0 | 6 |
| " | 0.25 | 14 | — | — | — | 2 | — | — | — | 0 | 3 |
| " | 0.125 | 14 | — | — | — | 0 | — | — | — | 0 | 3 |
| " | 8 | 21 | — | — | — | | | | | | |
| " | 2 | 21 | — | — | — | | | | | | |
| " | 1 | 21 | 9 | 4 | 5 | | | | | | |
| " | 0.5 | 21 | 5 | 4 | 0 | | | | | | |
| " | 0.25 | 21 | 2 | 2 | 0 | | | | | | |
| " | 0.125 | 21 | 2 | 0 | 0 | | | | | | |
| Product of Ex. 16 | 8 | 14 | NE | NE | 6 | | | | | | |
| " | 1 | 14 | NE | NE | 7 | 7 | | | | 6 | 6 |
| " | 0.5 | 14 | NE | 4 | 1 | 5 | | | | 6 | 8 |
| " | 0.25 | 14 | NE | 0 | 1 | 6 | | | | 6 | NE |
| " | 0.125 | 14 | 5 | 0 | 0 | 0 | | | | 0 | 0 |
| " | 8 | 21 | NE | NE | 8 | — | | | | — | — |
| " | 2 | 21 | | | | — | | | | — | — |
| " | 1 | 21 | NE | NE | 10 | 9 | | | | 7 | 5 |
| " | 0.5 | 21 | NE | 6 | 1 | 5 | | | | 7 | 10 |
| " | 0.25 | 21 | NE | 0 | 1 | 7 | | | | 7 | NE |
| " | 0.125 | 21 | 6 | 0 | 0 | 0 | | | | 0 | 0 |
| Product of Ex. 17 | 8 | 21 | NE | NE | 3 | — | | | | — | — |
| " | 2 | 21 | | | | | | | | | |
| " | 1 | 21 | 8 | 8 | 3.3 | 8 | | | | 6 | 5 |
| " | 0.5 | 21 | 7 | 0 | 3 | 3 | | | | 4 | 9 |
| " | 0.25 | 21 | 6 | 5 | 1.3 | 0 | | | | 0 | 0 |
| " | 0.125 | 21 | 6 | 0 | 1 | 0 | | | | 0 | 0 |
| Product of Ex. | 8 | 14 | NE | NE | 3 | — | | | | — | — |
| " | 2 | 14 | | | | — | | | | — | — |
| " | 1 | 14 | 6 | 5 | 1 | 7 | | | | 4 | 5 |
| " | 0.5 | 14 | 6 | 0 | 0 | 0 | | | | 1 | 9 |
| " | 0.25 | 14 | 6 | 6 | 0 | 0 | | | | 0 | 0 |
| " | 0.125 | 14 | 5 | 0 | 0 | 0 | | | | 0 | 0 |
| Product of Ex. 18 | 8 | 14 | 9 | NE | 0 | | | | | | |
| " | 8 | 21 | 0 | 0 | 0 | | | | | | |
| Product of Ex. | 8 | 14 | 8 | 9 | 0 | | | | | | |
| " | 2 | 14 | 2 | 4 | 0 | | | | | | |

TABLE I-continued

Injury Rating - Pre-Emergence

| Test Compound | Rate | Time After Treatment | | | | |
|---|---|---|---|---|---|---|
| " | 1 | 14 | 0 | 0 | 0 | |
| Product of Ex. 19 | 8 | 21 | 9 | 10 | 2 | |
| " | 2 | 21 | 0 | 1 | 2 | |
| " | 1 | 21 | 0 | 0 | 3 | |
| Product of Ex. 22 | 8 | 14 | — | — | — | |

| | | | | | | | | | | |
|---|---|---|---|---|---|---|---|---|---|---|
| " | 1 | 14 | NE | 2 | 3 | 6 | | | NE | NE |
| " | 0.5 | 14 | NE | 0 | 0 | 0 | | | 1 | 1 |
| " | 0.25 | 14 | 5 | 0 | 0 | 0 | | | 0 | 0 |
| " | 0.125 | 14 | 4 | 0 | 0 | 0 | | | 0 | 0 |
| " | 8 | 21 | NE | NE | 6 | — | | | — | — |
| " | 2 | 21 | | | | | | | — | — |
| " | 1 | 21 | NE | 3 | 2 | 6 | | | 0 | 0 |
| " | 0.5 | 21 | 10 | 0 | 1 | 0 | | | 1 | 0 |
| " | 0.25 | 21 | 4 | 0 | 0 | 0 | | | 0 | 0 |
| " | 0.125 | 21 | 4 | 0 | 0 | 0 | | | 0 | 0 |

| TEST COMPOUND | RATE lbs/Acre | TIME AFTER TREAT-MENT (Days) | RICE | SOYB | COTN | SORG | PTBN | CORN | ABLUE | QKGS | ALFA | OAT | SPGT |
|---|---|---|---|---|---|---|---|---|---|---|---|---|---|
| Product of Ex. 3 | 8 | 14 | — | — | — | — | — | — | | — | — | — | — |
| " | 2 | 14 | — | — | — | — | — | — | | — | — | — | — |
| " | 1 | 14 | 9 | 1 | 6 | 8 | 6 | 5 | | 4 | 4.3 | 7 | 10 |
| " | 0.5 | 14 | 9 | 1 | 1 | 6.2 | 6 | 5.3 | | 4 | 3.3 | 4 | 10 |
| " | 0.25 | 14 | 6.3 | 1 | 0 | 4 | 0 | 3 | | NE | 2 | 2.3 | 9 |
| " | 0.125 | 14 | 2.3 | 1 | 2 | 3.3 | 1 | 2 | | 2 | 1 | 1 | 9 |
| " | 8 | 21 | — | — | — | — | — | — | | — | — | — | — |
| " | 2 | 21 | — | — | — | — | — | — | | — | — | — | — |
| " | 1 | 21 | 6 | .3 | 4.3 | 7.3 | 5.3 | 4.3 | 10 | 8 | 4.3 | 8 | 10 |
| " | 0.5 | 21 | 8 | 0 | 0 | 9 | 2 | 4.3 | NE | 3 | 3 | 4 | 10 |
| " | 0.25 | 21 | 3.3 | 1 | 0 | 4.3 | 1 | 1 | 9.2 | 3 | 2 | 1.3 | 8 |
| " | 0.125 | 21 | 2 | 0 | 1 | 2.3 | .3 | 0 | 7 | 0 | 0 | 0 | 8 |
| Product of Ex. 8 | 8 | 14 | — | — | — | — | — | — | | — | — | — | — |
| " | 2 | 14 | NE | 6 | 9 | 9 | 8 | 7 | | 10 | 6 | 7 | NE |
| " | 1 | 14 | NE | 2 | 3 | 10 | 6 | 7 | | 10 | 3 | 6 | NE |
| " | 0.5 | 14 | 6 | 1 | 4 | 9 | 3 | 6 | | 10 | 2 | 6 | 10 |
| " | 0.25 | 14 | 5 | 1 | 0 | 5 | 3 | 4 | | 7 | 1 | 4 | 10 |
| " | 0.125 | 14 | NE | 0 | 2 | 4 | 1 | 4 | | 4 | 2 | 2 | 9 |
| " | 8 | 14 | — | — | — | — | — | — | | — | — | — | — |
| " | 2 | 14 | NE | 5 | 9 | 10 | 9 | 8 | | NE | 5 | 9 | NE |
| " | 1 | 14 | 10 | 2 | 3 | 10 | 7 | 7 | | 10 | 2 | 8 | 10 |
| " | 0.5 | 14 | 10 | 1 | 3 | 9 | 2 | 6 | | NE | 0 | 6 | 10 |
| " | 0.25 | 14 | 5 | 1 | 1 | 6 | 2 | 2 | | 8 | 0 | 3 | 10 |
| " | 0.125 | 14 | 7 | 0 | 2 | 4 | 2 | 0 | | 5 | 0 | 0 | 9 |
| Product of Ex. 10 | 8 | 14 | — | — | — | — | — | — | | — | — | — | — |
| " | 2 | 14 | NE | 8 | 7 | 9 | 2 | — | | NE | 4 | 7 | NE |
| " | 1 | 14 | NE | 2 | NE | 9 | 5 | — | | 10 | 2 | 6 | 9 |
| " | 0.5 | 14 | NE | 0 | 2 | 9 | 7 | — | | 10 | 0 | 6 | NE |
| " | 0.25 | 14 | 9 | 0 | 2 | 6 | 0 | — | | 9 | 0 | 2 | 10 |
| " | 0.125 | 14 | — | — | — | — | — | — | | — | — | — | — |
| " | 8 | 21 | — | — | — | — | — | — | | — | — | — | — |
| " | 2 | 21 | NE | 8 | 8 | NE | 0 | 7 | | NE | 2 | 10 | NE |
| " | 1 | 21 | NE | 0 | NE | 10 | 3 | 6 | | NE | 1 | 9 | NE |
| " | 0.5 | 21 | 9 | 0 | 3 | 9 | 6 | 2 | | NE | 0 | 9 | NE |
| " | 0.25 | 21 | 8 | 0 | 2 | 4 | 0 | 0 | | 6 | 0 | 2 | NE |
| " | 0.125 | 21 | — | — | — | — | — | — | | — | — | — | — |
| Product of Ex. 11 | 8 | 21 | — | — | — | NE | — | — | | — | — | — | — |
| " | 2 | 21 | NE | 1 | NE | NE | 7 | 4 | | NE | 0 | 9 | 9 |
| " | 1 | 21 | NE | 0 | 0 | 9 | 0 | 2 | | 5 | 0 | 3 | 10 |
| " | 0.5 | 21 | 9 | 0 | 0 | 7 | 0 | 0 | | 6 | 0 | 3 | NE |
| " | 0.25 | 21 | 0 | 0 | 0 | 2 | 0 | 0 | | 0 | 0 | 0 | 3 |
| " | 0.125 | 21 | — | — | — | — | — | — | | — | — | — | — |
| Product of Ex. 13 | 8 | 14 | — | — | — | — | — | — | | | | | |
| " | 2 | 14 | — | — | — | — | — | — | | | | | |
| " | 1 | 14 | NE | 3 | 0 | — | — | — | | | | | |
| " | 0.5 | 14 | 7 | 2 | 0 | — | — | — | | | | | |
| " | 0.25 | 14 | 5 | 2 | 0 | — | — | — | | | | | |
| " | 0.125 | 14 | 8 | 3 | 0 | — | — | — | | | | | |
| Product of Ex. 16 | 1 | 14 | 8 | 2 | NE | 6 | 0 | 6 | | 9 | 0 | 3 | NE |
| " | 0.5 | 14 | NE | 0 | NE | 5 | 0 | 3 | | 9 | 0 | 3 | NE |
| " | 0.25 | 14 | 8 | 0 | 0 | 4 | 0 | 0 | | 6 | 0 | 0 | NE |
| " | 0.125 | 14 | 3 | 0 | 0 | 0 | 0 | 0 | | 0 | 0 | 0 | NE |
| " | 8 | 21 | — | — | — | — | — | — | | — | — | — | — |
| " | 2 | 21 | — | — | — | — | — | — | | — | — | — | — |
| " | 1 | 21 | NE | 4 | NE | 6 | 1 | 5 | | 10 | 1 | 4 | NE |
| " | 0.5 | 21 | NE | 1 | NE | 6 | 0 | 3 | | 10 | 1 | 4 | NE |
| " | 0.25 | 21 | 10 | 0 | 0 | 3 | 0 | 0 | | 5 | 1 | 0 | NE |
| " | 0.125 | 21 | 3 | 0 | 0 | 0 | 0 | 0 | | 0 | 1 | 0 | NE |
| Product of Ex. 17 | 8 | 21 | — | — | — | — | — | — | | — | — | — | — |
| " | 2 | 21 | — | — | — | — | — | — | | — | — | — | — |

TABLE I-continued

Injury Rating - Pre-Emergence

| | | | | | | | | | | | | | |
|---|---|---|---|---|---|---|---|---|---|---|---|---|---|
| " | 1 | 21 | 6 | 1 | NE | 5 | NE | 4 | | 6 | 0 | 3 | NE |
| " | 0.5 | 21 | 5 | 1 | 2 | 2 | 0 | 2 | | 0 | 0 | 0 | NE |
| " | 0.25 | 21 | 0 | 0 | 0 | 2 | 0 | 0 | | 0 | 0 | 0 | NE |
| " | 0.125 | 21 | 0 | 0 | 0 | 0 | 0 | 0 | | 0 | 0 | 0 | NE |
| Product of Ex. | 8 | 14 | — | — | — | — | — | — | | — | — | — | — |
| " | 2 | 14 | — | — | — | — | — | — | | — | — | — | — |
| " | 1 | 14 | 5 | 0 | NE | 5 | NE | 4 | | 5 | 2 | 1 | NE |
| " | 0.5 | 14 | 6 | 0 | 0 | 3 | 0 | 0 | | 0 | 0 | 0 | NE |
| " | 0.25 | 14 | 2 | 0 | 0 | 3 | 0 | 0 | | 0 | 0 | 0 | NE |
| " | 0.125 | 14 | 0 | 0 | 0 | 0 | 0 | 0 | | 0 | 0 | 0 | NE |
| Product of Ex. 22 | 1 | 14 | 6 | 0 | 0 | 4 | 5 | 3 | | 10 | 0 | 3 | NE |
| " | 0.5 | 14 | 7 | 0 | 0 | 2 | 4 | 0 | | 0 | 0 | 0 | NE |
| " | 0.25 | 14 | 0 | 0 | 0 | 0 | 0 | 0 | | 0 | 0 | 0 | NE |
| " | 0.125 | 14 | 0 | 0 | 0 | 0 | 0 | 0 | | 0 | 0 | 0 | 5 |
| " | 8 | 21 | — | — | — | — | — | — | | — | — | — | — |
| " | 2 | 21 | — | — | — | — | — | — | | — | — | — | — |
| " | 1 | 21 | 6 | 4 | 0 | 4 | 6 | 3 | | 10 | 0 | 4 | NE |
| " | 0.5 | 21 | 8 | 0 | 0 | 2 | 6 | 0 | | 0 | 0 | 0 | NE |
| " | 0.25 | 21 | 2 | 0 | 0 | 0 | 2 | 0 | | 0 | 0 | 0 | NE |
| " | 0.125 | 21 | 0 | 0 | 0 | 0 | 0 | 0 | | 0 | 0 | 0 | 0 |

TABLE II

Injury Rating - Post-Emergence

| TEST COMPOUND | RATE lbs/Acre | TIME AFTER TREATMENT (Days) | YNSG | WOAT | JMWD | VTLF | JNGS | PIGW | WMSTD | YLFX | BNGS |
|---|---|---|---|---|---|---|---|---|---|---|---|
| Product of Ex.3 | 8 | 14 | 0 | 5 | 8 | — | 9 | 3 | 8 | 8 | 10 |
| " | 2 | 14 | 0 | 4 | 4 | — | 7 | 2 | 5 | 6 | 10 |
| " | 1 | 14 | 0 | 4.3 | 3 | 6 | 7 | 3 | 3 | 7 | 8 |
| " | 0.5 | 14 | — | 6 | 2 | 6 | 7 | 3 | 2 | 7 | 8 |
| " | 0.25 | 14 | — | 0 | 2 | 5 | 6 | 3 | 2 | 6 | 8 |
| " | 0.125 | 14 | — | 0 | 1 | 5 | 6 | 1 | 1 | 2 | 7 |
| Product of Ex. 8 | 8 | 14 | 7 | 7 | 5 | — | 9 | 10 | 6 | 8 | 10 |
| " | 2 | 14 | 3 | 7 | 3 | 6 | 8 | 4 | 5 | 9 | 7 |
| " | 1 | 14 | 0 | 6 | 3 | 6 | 8 | 3 | 3 | 8 | 7 |
| " | 0.5 | 14 | — | 2 | 2 | 6 | 5 | 0 | 4 | 3 | 6 |
| " | 0.25 | 14 | — | 0 | 0 | 6 | 0 | 0 | 2 | 2 | 6 |
| " | 0.125 | 14 | — | — | — | — | — | — | — | — | — |
| Product of Ex. 10 | 8 | 14 | 5 | 8 | 10 | — | 10 | 10 | 4 | 9 | 10 |
| " | 2 | 14 | 2 | 5 | 6 | 8 | 8 | 5 | 4 | 8 | 10 |
| " | 1 | 14 | 0 | 3 | 2 | 7 | 7 | 1 | 3 | 8 | 8 |
| " | 0.5 | 14 | — | 0 | 2 | 7 | 7 | 0 | 3 | 6 | 6 |
| " | 0.25 | 14 | — | 0 | 2 | 4 | 1 | 0 | 1 | 0 | 2 |
| " | 0.125 | 14 | — | — | — | — | — | — | — | — | — |
| Product of Ex. 11 | 8 | 14 | 2 | 7 | 8 | — | 10 | 10 | 5 | 10 | 10 |
| " | 2 | 14 | 1 | 3 | 5 | 8 | 8 | 8 | 3 | 8 | 10 |
| " | 1 | 14 | 0 | 1 | 5 | 6 | 8 | 3 | 1 | 7 | 8 |
| " | 0.5 | 14 | — | 0 | 4 | 4 | 2 | 3 | 0 | 4 | 6 |
| " | 0.25 | 14 | — | 0 | 3 | 4 | 0 | 0 | 1 | 0 | 3 |
| " | 0.125 | 14 | — | — | — | — | — | — | — | — | — |
| Product of Ex. 12 | 8 | 14 | 9 | 10 | 10 | — | 3 | 10 | 10 | 5 | 10 |
| " | 2 | 14 | 8 | 9 | 9 | — | 2 | 6 | 7 | 4 | 1 |
| " | 1 | 14 | 6 | 7 | 7 | — | 0 | 3 | 3 | 2 | 0 |
| " | 0.5 | 14 | — | — | — | — | — | — | — | — | — |
| " | 0.25 | 14 | — | — | — | — | — | — | — | — | — |
| " | 0.125 | 14 | — | — | — | — | — | — | — | — | — |
| Product of Ex. 13 | 8 | 14 | 2 | 5 | 0 | — | 8 | 10 | 2 | 8 | 8 |
| " | 2 | 14 | 0 | 2 | 0 | — | 7 | 3 | 0 | 7 | 8 |
| " | 1 | 14 | 0 | 1 | 0 | — | 7 | 2 | 0 | 7 | 7 |
| " | 0.5 | 14 | — | — | — | — | — | — | — | — | — |
| " | 0.25 | 14 | — | — | — | — | — | — | — | — | — |
| " | 0.125 | 14 | — | — | — | — | — | — | — | — | — |
| Product of Ex. 16 | 8 | 14 | 0 | 5 | 4 | — | 6 | 0 | 7 | 6 | 7 |
| Product of Ex. 17 | 8 | 14 | 0 | 4 | 2 | | 5 | 2 | 4 | 7 | 7 |
| Product of Ex. 18 | 8 | 14 | 0 | 0 | 2 | | 0 | 0 | 2 | 3 | 7 |
| Product of Ex. 19 | 4 | 14 | 0 | 0 | 10 | — | 10 | 9 | 10 | 8 | 10 |
| " | 2 | 14 | 0 | 0 | 10 | 4 | 4 | 5 | 8 | 3 | 9 |
| " | 1 | 14 | 0 | 0 | 7 | 4 | 4 | 0 | 4 | 4 | 3 |
| " | 0.5 | 14 | — | 0 | 4 | 3 | 0 | 0 | 0 | 2 | 0 |
| " | 0.25 | 14 | — | 0 | 3 | 2 | 0 | 0 | 0 | 0 | 0 |
| " | 0.125 | 14 | — | — | — | — | — | — | — | — | — |
| Product of Ex. 22 | 8 | 14 | 0 | 4 | 3 | — | 5 | 1 | 4 | 5 | 6 |
| " | 2 | 14 | 8 | 9 | 9 | — | 2 | 6 | 7 | 4 | 1 |
| " | 1 | 14 | 6 | 7 | 7 | — | 0 | 3 | 3 | 2 | 0 |
| " | 0.5 | 14 | — | — | — | — | — | — | — | — | — |
| " | 0.25 | 14 | — | — | — | — | — | — | — | — | — |
| " | 0.125 | 14 | — | — | — | — | — | — | — | — | — |

TABLE II-continued

| | | | Injury Rating - Post-Emergence | | | | | | | | |
|---|---|---|---|---|---|---|---|---|---|---|---|
| TEST COMPOUND | RATE lbs/Acre | TIME AFTER TREATMENT (Days) | Weed Species | | | | | | | | |
| | | | CBGS | CTGS | MNGY | BDWD | MBLUE | TFES | PYRE | SUBT | WHT |
| Product of Ex. 3 | 8 | 14 | 9 | — | 7 | 0 | — | — | — | — | — |
| " | 2 | 14 | 8 | — | 2 | 0 | — | — | — | — | — |
| " | 1 | 14 | 8 | 2 | 4.3 | 1 | — | — | — | 1 | 4 |
| " | 0.5 | 14 | 8 | 1 | 3 | 2 | — | — | — | 1 | 3 |
| " | 0.25 | 14 | 8 | 1 | 2 | 0 | — | — | — | 0 | 5 |
| " | 0.125 | 14 | 6 | 0 | 1 | 0 | — | — | — | 0 | 0 |
| Product of Ex. 8 | 8 | 14 | 8 | — | 5 | 6 | — | — | — | — | — |
| " | 2 | 14 | 9 | 4 | 5 | 5 | — | — | — | 2 | 5 |
| " | 1 | 14 | 8 | 3 | 4 | 5 | — | — | — | 1 | 7 |
| " | 0.5 | 14 | 7 | 0 | 4 | 0 | — | — | — | 0 | 5 |
| " | 0.25 | 14 | 0 | 0 | 4 | 0 | — | — | — | 0 | 2 |
| " | 0.125 | 14 | — | — | — | — | — | — | — | — | — |
| Product of Ex. 10 | 8 | 14 | 1 | — | 9 | 5 | — | — | — | — | — |
| " | 2 | 14 | 6 | — | 6 | 3 | — | — | — | 2 | 7 |
| " | 1 | 14 | 5 | — | 3 | 2 | — | — | — | 1 | 5 |
| " | 0.5 | 14 | 0 | — | 4 | 0 | — | — | — | 0 | 2 |
| " | 0.25 | 14 | 0 | — | 3 | 0 | — | — | — | 0 | 0 |
| " | 0.125 | 14 | — | — | — | — | — | — | — | — | — |
| Product of Ex. 11 | 8 | 14 | 10 | — | 9 | 5 | — | — | — | — | — |
| " | 2 | 14 | 9 | 3 | 6 | 4 | — | — | — | 2 | 7 |
| " | 1 | 14 | 8 | 1 | 5 | 3 | — | — | — | 1 | 2 |
| " | 0.5 | 14 | 9 | 0 | 4 | 0 | — | — | — | 0 | 0 |
| " | 0.25 | 14 | 7 | 0 | 3 | 0 | — | — | — | 0 | 0 |
| " | 0.125 | 14 | — | — | — | — | — | — | — | — | — |
| Product of Ex. 12 | 8 | 14 | 10 | 10 | 10 | 10 | | | | | |
| " | 2 | 14 | 10 | 10 | 6 | 5 | | | | | |
| " | 1 | 14 | 2 | 2 | 0 | 1 | | | | | |
| " | 0.5 | 14 | — | — | — | — | | | | | |
| " | 0.25 | 14 | — | — | — | — | | | | | |
| " | 0.125 | 14 | — | — | — | — | | | | | |
| Product of Ex. 13 | 8 | 14 | 9 | — | 8 | 8 | | | | | |
| " | 2 | 14 | 9 | — | 4 | 3 | | | | | |
| " | 1 | 14 | 8 | — | 3 | 0 | | | | | |
| " | 0.5 | 14 | — | — | — | — | | | | | |
| " | 0.25 | 14 | — | — | — | — | | | | | |
| " | 0.125 | 14 | — | — | — | — | | | | | |
| Product of Ex. 16 | 8 | 14 | 3 | | 4 | 6 | | | | | |
| Product of Ex. 17 | 8 | 14 | 4 | | 5 | 5 | | | | | |
| Product of Ex. 18 | 8 | 14 | 1 | | 3 | 1 | | | | | |
| Product of Ex. 19 | 8 | 14 | | | | 10 | | | | | — |
| " | 4 | 14 | 10 | — | 5 | | | | | | |
| " | 2 | 14 | 7 | 0 | 6 | 4 | | | | | 1 |
| " | 1 | 14 | 7 | 0 | 4 | 0 | | | | | 0 |
| " | 0.5 | 14 | 4 | 0 | 4 | 0 | | | | | 0 |
| " | 0.25 | 14 | 0 | 0 | 1 | 0 | | | | | 0 |
| " | 0.125 | 14 | — | — | — | — | | | | | — |
| Product of Ex. 22 | 8 | 14 | 2 | 10 | 4 | 4 | | | | | |
| " | 2 | 14 | 10 | 10 | 6 | 5 | | | | | |
| " | 1 | 14 | 2 | 2 | 0 | 1 | | | | | |
| " | 0.5 | 14 | — | — | — | — | | | | | |
| " | 0.25 | 14 | — | — | — | — | | | | | |
| " | 0.125 | 14 | — | — | — | — | | | | | |

| TEST COMPOUND | RATE lbs/Acre | TIME AFTER TREATMENT (Days) | Weed Species | | | | | | | | |
|---|---|---|---|---|---|---|---|---|---|---|---|
| | | | RICE | SOYB | COTN | SORG | PTBN | CORN | OKGS | ALFA | OAT | SPGT |
| Product of Ex. 3 | 8 | 14 | — | 8 | — | — | — | — | — | — | — | — |
| " | 2 | 14 | — | 6 | — | — | — | — | — | — | — | — |
| " | 1 | 14 | 6 | 6 | 4 | 7 | 3 | 7 | 6 | 3 | 5 | 6 |
| " | 0.5 | 14 | 3 | 1 | 2 | 5 | 1 | 6 | 4 | 2 | 3 | 7 |
| " | 0.25 | 14 | 3 | 0 | 2 | 2 | 0 | 3 | 3 | 1 | 2 | 3 |
| " | 0.125 | 14 | 1 | 0 | 1 | 3 | 0 | 2 | 2 | 1 | 1 | 6 |
| Product of Ex. 8 | 8 | 14 | — | 9 | — | — | — | — | — | — | — | — |
| " | 2 | 14 | 7 | 2 | 3 | 9 | — | 7 | 3 | 2 | 7 | 9 |
| " | 1 | 14 | 5 | 1 | 3 | 8 | — | 6 | 7 | 1 | 5 | 9 |
| " | 0.5 | 14 | 6 | 2 | 2 | 2 | — | 4 | 6 | 0 | 6 | 6 |
| " | 0.25 | 14 | 0 | 0 | 0 | 1 | — | 1 | 4 | 0 | 0 | 3 |
| " | 0.125 | 14 | — | — | — | — | — | — | — | — | — | — |
| Product of Ex. 10 | 8 | 14 | — | 8 | — | — | — | — | — | — | — | — |
| " | 2 | 14 | 3 | 4 | 1 | 7 | — | 4 | 6 | 2 | 3 | 8 |
| " | 1 | 14 | 6 | 3 | 0 | 2 | — | 4 | 5 | 1 | 2 | 8 |
| " | 0.5 | 14 | 4 | 0 | 0 | 1 | — | 2 | 7 | 0 | 0 | 6 |
| " | 0.25 | 14 | 0 | 0 | 0 | 0 | — | 0 | 5 | 0 | 0 | 4 |
| " | 0.125 | 14 | — | — | — | — | — | — | — | — | — | — |
| Product of Ex. 11 | 8 | 14 | — | 9 | — | — | — | — | — | — | — | — |
| " | 2 | 14 | 5 | 5 | 3 | 2 | — | 7 | 9 | 3 | 6 | 1 |
| " | 1 | 14 | 4 | 2 | 0 | 0 | — | 7 | 7 | 0 | 2 | 7 |

TABLE II-continued

| | | | Injury Rating - Post-Emergence | | | | | | | | | |
|---|---|---|---|---|---|---|---|---|---|---|---|---|
| " | 0.5 | 14 | 1 | 1 | 0 | 0 | — | 0 | 6 | 0 | 0 | 4 |
| " | 0.25 | 14 | 1 | 0 | 0 | 0 | — | 0 | 3 | 0 | 0 | 3 |
| " | 0.125 | 14 | — | — | — | — | — | — | — | — | — | — |
| Product of Ex. 12 | 8 | 14 | 0 | | | | | | | | | |
| " | 2 | 14 | 0 | | | | | | | | | |
| " | 1 | 14 | 0 | | | | | | | | | |
| " | 0.5 | 14 | — | | | | | | | | | |
| " | 0.25 | 14 | — | | | | | | | | | |
| " | 0.125 | 14 | — | | | | | | | | | |
| Product of Ex. 13 | 8 | 14 | 9 | | | | | | | | | |
| " | 2 | 14 | 9 | | | | | | | | | |
| " | 1 | 14 | 0 | | | | | | | | | |
| " | 0.5 | 14 | — | | | | | | | | | |
| " | 0.25 | 14 | — | | | | | | | | | |
| " | 0.125 | 14 | — | | | | | | | | | |
| Product of Ex. 16 | 8 | 14 | 4 | | | | | | | | | |
| Product of Ex. 17 | 8 | 14 | 5 | | | | | | | | | |
| Product of Ex. 18 | 8 | 14 | 3 | | | | | | | | | |
| Product of Ex. 19 | 8 | 14 | — | — | — | — | — | — | — | — | — | — |
| " | 2 | 14 | 0 | 0 | 0 | — | 2 | 7 | 4 | 0 | 0 | |
| " | 1 | 14 | 0 | 0 | 0 | 0 | 0 | 2 | 2 | 0 | 0 | |
| " | 0.5 | 14 | 0 | 0 | 0 | 0 | 0 | 0 | 0 | 0 | 0 | |
| " | 0.25 | 14 | 0 | 0 | 0 | 0 | 0 | 0 | 0 | 0 | 0 | |
| " | 0.125 | 14 | — | — | — | — | — | — | — | — | — | |
| Product of Ex. 22 | 8 | 14 | 2 | | | | | | | | | |
| " | 2 | 14 | 0 | | | | | | | | | |
| " | 1 | 14 | 0 | | | | | | | | | |
| " | 0.5 | 14 | — | | | | | | | | | |
| " | 0.25 | 14 | — | | | | | | | | | |
| " | 0.125 | 14 | — | | | | | | | | | |

I claim:

1. A compound of the formula

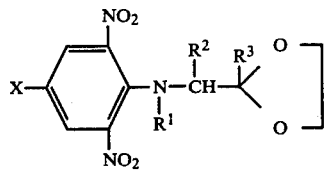

wherein $R^1$ is alkyl; $R^2$ and $R^3$ are independently selected from the group consisting of hydrogen and alkyl; and X is selected from the group consisting of alkyl and haloalkyl.

2. The compound of claim 1, N-propyl-N-1,3-dioxolan-2-ylmethyl-2,6-dinitro-4-trifluoromethylaniline.

3. The compound of claim 1, N-methyl-N-1,3-dioxolan-2-yl-methyl-2,6-dinitro-4-trifluoromethylaniline.

4. The compound of claim 1, N-ethyl-N-1,3-dioxolan-2-ylmethyl-2,6-dinitro-4-trifluoromethylaniline.

5. The compound of claim 1, N-ethyl-N-1,3-dioxolan-2-ylmethyl-2,6-dinitro-p-toluidine.

6. The compound of claim 1, N-propyl-N-1,3-dioxolan-2-ylmethyl-2,6-dinitro-p-toluidine.

7. The compound of claim 1, N-methyl-N-1,3-dioxolan-2-ylmethyl-2,6-dinitro-p-toluidine.

8. The compound of claim 1, N-isopropyl-N-1,3-dioxolan-2-ylmethyl-2,6-dinitro-4-trifluoromethylaniline.

9. The compound of claim 1, N-ethyl-N-1,3-dioxolan-2-ylmethyl-2,6-dinitro-4-t-butylaniline.

10. The compound of claim 1, N-propyl-N-1,3-dioxolan-2-ylmethyl-2,6-dinitro-4-t-butylaniline.

11. The compound of claim 1, N-ethyl-N-(2-methyl-1,3-dioxolan-2-yl)methyl-4-t-butyl-2,6-dinitroaniline.

12. A herbicidal composition comprising an inert carrier and, as an essential active ingredient, in a quantity toxic to weeds, a compound of claim 1.

13. A method of controlling weeds which comprises contacting said weeds with a herbicidal composition comprising an inert carrier and, as an essential active ingredient, in a quantity toxic to weeds, a compound of claim 1.

* * * * *